US012685438B2

(12) United States Patent
Zhou et al.

(10) Patent No.: US 12,685,438 B2
(45) Date of Patent: Jul. 21, 2026

(54) METHOD AND APPARATUS FOR DETECTING PENETRATION DEPTH OF RIBOFLAVIN IN CORNEA

(71) Applicant: EYE AND EAR NOSE AND THROAT HOSPITAL AFFILIATED TO FUDAN UNIVERSITY, Shanghai (CN)

(72) Inventors: Xingtao Zhou, Shanghai (CN); Jinhai Huang, Shanghai (CN); Cuizhi Wang, Shanghai (CN); Peijun Yao, Shanghai (CN); Tian Han, Shanghai (CN); Meiyan Li, Shanghai (CN)

(73) Assignee: EYE AND EAR NOSE AND THROAT HOSPITAL AFFILIATED TO FUDAN UNIVERSITY, Shanghai (CN)

( * ) Notice: Subject to any disclaimer, the term of this patent is extended or adjusted under 35 U.S.C. 154(b) by 277 days.

(21) Appl. No.: 18/709,522

(22) PCT Filed: Apr. 15, 2022

(86) PCT No.: PCT/CN2022/087001
§ 371 (c)(1),
(2) Date: May 13, 2024

(87) PCT Pub. No.: WO2023/092929
PCT Pub. Date: Jun. 1, 2023

(65) Prior Publication Data
US 2025/0000355 A1     Jan. 2, 2025

(30) Foreign Application Priority Data

Nov. 24, 2021     (CN) ......................... 202111405728.9

(51) Int. Cl.
A61B 3/10 (2006.01)
A61B 3/00 (2006.01)
G06T 7/00 (2017.01)

(52) U.S. Cl.
CPC .............. *A61B 3/0025* (2013.01); *A61B 3/10* (2013.01); *G06T 7/0012* (2013.01); *G06T 2207/10024* (2013.01); *G06T 2207/30041* (2013.01)

(58) Field of Classification Search
CPC ......... A61B 3/0025; A61B 3/10; A61B 3/107; G06T 7/0012; G06T 2207/10024; G06T 2207/30041; G06T 7/11; A61P 27/02
See application file for complete search history.

(56) References Cited

U.S. PATENT DOCUMENTS

2014/0194957 A1*   7/2014  Rubinfeld .............. A61N 5/062
                                                         607/90

FOREIGN PATENT DOCUMENTS

CN       108470348 A  *  8/2018   ............... G06T 7/13
CN       111861977 A  *  10/2020  ............... G06T 7/11

OTHER PUBLICATIONS

Pandey, A. and Pati, U.C. (2017), "Development of saliency-based seamless image compositing using hybrid blending (SSICHB)." IET Image Processing, 11: 433-442. https://doi.org/10.1049/iet-ipr.2016.0754 (Year: 2017).*

* cited by examiner

*Primary Examiner* — Stephen R Koziol
*Assistant Examiner* — Samuel D Baynes
(74) *Attorney, Agent, or Firm* — Leong C. Lei

(57) ABSTRACT

A method for detecting a penetration depth of riboflavin in a cornea includes acquiring an optical section of RGB colors and converting it into an image in a CIEL*a*b* color space, extracting a luminance component L* in the CIEL*a*b*

(Continued)

color space, performing binarization and Blob analysis to obtain a non-corneal-region-free image; based on the non-corneal-region-free image and the luminance component L* image, extracting boundary points of anterior and posterior corneal surfaces and performing curve fitting, so as to obtain anterior and posterior corneal surface curves; performing image fusion on the anterior and posterior corneal surface curves into the CIEL*a*b* color space to obtain a cornea-only CIEL*a*b* color image; in the cornea-only CIEL*a*b* color image, locating a riboflavin-penetrating region and partitioning the riboflavin-penetrating region into riboflavin-penetrating sites, and performing curve fitting and noise reduction on the riboflavin-penetrating sites to obtain riboflavin the penetration depth and the anterior and posterior curves.

9 Claims, 5 Drawing Sheets acquiring an optical section of RGB colors, converting the optical section of the RGB colors into an image in a CIEL*a*b* color space, and in extracting a luminance component L* in the CIEL*a*b* color space, so as to obtain a luminance component L* image, and then performing binarization and Blob analysis on the luminance component L* image, so as to obtain a non-corneal-region-free image that does not contain any part related to any non-corneal region

S1 based on the non-corneal-region-free image and the luminance component L* image, using a gradient method to extract all anterior boundary points on an anterior corneal surface of the cornea and all posterior boundary points on a posterior corneal surface of the cornea, and performing curve fitting on all of the anterior boundary points and all of the posterior boundary points, respectively, so as to obtain an anterior curve of the anterior corneal surface and a posterior curve of the anterior corneal surface

S2 performing image fusion of the anterior curve and the posterior curve into the CIEL*a*b* color space, so as to obtain a cornea-only CIEL*a*b* color image that covers only the cornea, and in the cornea-only CIEL*a*b* color image, locating a riboflavin-penetrating region and partitioning the riboflavin-penetrating region into riboflavin-penetrating sites, and performing curve fitting and noise reduction on all of the riboflavin-penetrating sites, so as to obtain riboflavin the penetration depth and the anterior and posterior curves

METHOD AND APPARATUS FOR DETECTING PENETRATION DEPTH OF RIBOFLAVIN IN CORNEA

BACKGROUND OF THE INVENTION

1. Technical Field

The present invention relates to computer-based image processing, and more particularly to a method and an apparatus for detecting a penetration depth of riboflavin in a cornea.

2. Description of Related Art

Corneal collagen cross-linking (CXL) is the latest keratoplasty first introduced in the late 20$^{th}$ century and clinically applied in the early 21$^{st}$ century. It is recognized as one of the most important therapeutical innovations in the modern ophthalmology. CXL increases mechanical strength, biomechanical stability, and ectasia resistance of corneas through covalent bonding between corneal collagen fibrils induced by unstable active oxygen ions that are generated when riboflavin used as a photosensitizer is irradiated by ultraviolet A of 370 nm.

In recent years, CXL has been increasingly used in treating corneal diseases like keratoconus, corneal ectasia and refractory corneal ulcer after excimer laser surgery, keratitis, and corneal melting with the prerequisite that only when riboflavin reaches a predetermined penetration depth into the cornea can UV A irradiation be applied. In other words, the penetration depth of riboflavin in corneas is one of the essentials of successful treatment.

For making riboflavin penetrate corneas faster and deeper, many manufacturers have developed riboflavin-based photosensitizers of different formulas. However, how to qualitatively and quantitatively ascertain the penetration depth of riboflavin is a new topic to explore and the vacancy for measuring methods in the prior art also has to be filled.

SUMMARY OF THE INVENTION

The objective of embodiments of the present invention is to provide a method and an apparatus for detecting a penetration depth of riboflavin in a cornea, which quantitatively ascertain a penetration depth of riboflavin in a cornea in an intuitive and accurate manner.

To achieve the foregoing objective, one embodiment of the present invention provides a method for detecting a penetration depth of riboflavin in a cornea. The method comprises steps of:

Step S1: acquiring an optical section of RGB colors, converting the optical section of the RGB colors into an image in a CIEL*a*b* color space, and in extracting a luminance component L* in the CIEL*a*b* color space, so as to obtain a luminance component L* image, and then performing binarization and Blob analysis on the luminance component L* image, so as to obtain a non-corneal-region-free image that does not contain any part related to any non-corneal region;

Step S2: based on the non-corneal-region-free image and the luminance component L* image, using a gradient method to extract all anterior boundary points on an anterior corneal surface of the cornea and all posterior boundary points on a posterior corneal surface of the cornea, and performing curve fitting on all of the anterior boundary points and all of the posterior boundary points, respectively, so as to obtain an anterior curve of the anterior corneal surface and a posterior curve of the anterior corneal surface; and Step S3: performing image fusion of the anterior curve and the posterior curve into the CIEL*a*b* color space, so as to obtain a cornea-only CIEL*a*b* color image that covers only the cornea, and in the cornea-only CIEL*a*b* color image, locating a riboflavin-penetrating region and partitioning the riboflavin-penetrating region into riboflavin-penetrating sites, and performing curve fitting and noise reduction on all of the riboflavin-penetrating sites, so as to obtain riboflavin the penetration depth and the anterior and posterior curves.

Therein, the optical section of the RGB colors in Step S1 is first converted into a CIE-XYZ color space and then converted into the CIEL*a*b* color space.

Therein, conversion of the optical section between the CIE-XYZ color space and the RGB color space is expressed in Equation (1):

$$\begin{pmatrix} X \\ Y \\ Z \end{pmatrix} = \begin{pmatrix} 0.412453 & 0.357580 & 0.180423 \\ 0.212671 & 0.715160 & 0.072169 \\ 0.019334 & 0.119193 & 0.950227 \end{pmatrix} * \begin{pmatrix} R \\ G \\ B \end{pmatrix}. \tag{1}$$

Therein, a conversion relation between the CIEL*a*b* color space and the CIE-XYZ color space is expressed in Equation (2):

$$L^* = \begin{cases} 116 * \sqrt[3]{\dfrac{Y}{Y_n}} - 16 & \left(\dfrac{Y}{Y_n} > 0.008856\right) \\ 903.25 * \dfrac{Y}{Y_n} & \left(\dfrac{Y}{Y_n} \le 0.008856\right) \end{cases} \tag{2}$$

$$a^* = 500\left[f\left(\frac{X}{X_n}\right) - f\left(\frac{Y}{Y_n}\right)\right]$$

$$b^* = 200\left[f\left(\frac{Y}{Y_n}\right) - f\left(\frac{Z}{Z_n}\right)\right]$$

where, if t>0.008856, f(t)=

$$\sqrt[3]{t}$$

; otherwise f(t)=7.787*t; and when a CIE standard light source D65 is used, $X_n$=94.81, $Y_n$=100.00, $Z_n$=107.304.

Therein, the Step S3 comprises:

in the non-corneal-region-free image, based on a midpoint of an X axis as a starting point, locating a corresponding anterior corneal surface boundary, drawing a line in the luminance component L* image correspondingly, and further using the gradient method, so as to obtain actual boundary points along the drawn line as all the anterior boundary points;

in the non-corneal-region-free image, based on the midpoint of the X axis as a starting point, locating a corresponding posterior corneal surface boundary, drawing a line in the luminance component L* image correspondingly, and further using the gradient method, so as to obtain actual boundary points along the drawn line as all the posterior boundary points; and performing polynomial fitting based on a least squares method on both of all the anterior boundary points and all the posterior boundary points, so as to obtain the anterior curve and the posterior curve.

Therein, the Step S4 comprises:

using a minimum method to perform image fusion of the anterior curve and the posterior curve into the CIEL\*a\*b\* color space, so as to obtain the cornea-only CIEL\*a\*b\* color image;

in the cornea-only CIEL\*a\*b\* color image, locating the riboflavin-penetrating region that divides each of superior and inferior corneal surfaces into two parts;

using a K-mean clustering algorithm to partition the riboflavin-penetrating region, so as to obtain the riboflavin-penetrating sites; and performing the curve fitting and the noise reduction on all the riboflavin-penetrating sites, so as to obtain the penetration depth and the anterior and posterior curves.

Therein, the optical section of the RGB colors in Step S1 is acquired using a slit lamp.

Another embodiment of the present invention provides an apparatus detecting a penetration depth of riboflavin in a cornea. The apparatus comprises:

an image converting and analyzing unit, for acquiring an optical section of RGB colors, converting the optical section of the RGB colors into an image in a CIEL\*a\*b\* color space, and in extracting a luminance component L\* in the CIEL\*a\*b\* color space, so as to obtain a luminance component L\* image, and then performing binarization and Blob analysis on the luminance component L\* image, so as to obtain a non-corneal-region-free image that does not contain any part related to any non-corneal region;

an image outline curve fitting unit, for, based on the non-corneal-region-free image and the luminance component L\* image, using a gradient method to extract all anterior boundary points on an anterior corneal surface of the cornea and all posterior boundary points on a posterior corneal surface of the cornea, and performing curve fitting on all of the anterior boundary points and all of the posterior boundary points, respectively, so as to obtain an anterior curve of the anterior corneal surface and a posterior curve of the anterior corneal surface; and a riboflavin penetration depth acquiring unit, for performing image fusion of the anterior curve and the posterior curve into the CIEL\*a\*b\* color space, so as to obtain a cornea-only CIEL\*a\*b\* color image that covers only the cornea, and in the cornea-only CIEL\*a\*b\* color image, locating a riboflavin-penetrating region and partitioning the riboflavin-penetrating region into riboflavin-penetrating sites, and performing curve fitting and noise reduction on all of the riboflavin-penetrating sites, so as to obtain riboflavin the penetration depth and the anterior and posterior curves.

Therein, the optical section of the RGB colors is acquired using a slit lamp.

Implementation of the embodiments of the present invention provides the following beneficial effects:

In the present invention, an optical section is acquired using a slit lamp that is commonly used for ophthalmologic examinations. Then the acquired RGB color image is converted into the CIEL\*a\*b\* color space. The luminance component L\* is extracted for binarization and Blob analysis, so as to extract the region showing the cornea. Afterward, the exact boundaries of the anterior and posterior corneal surfaces are located using the gradient method and curve fitting is performed. The result is fused into the CIEL\*a\*b\* color space to provide a CIEL\*a\*b\* color image covering only the cornea. At last, riboflavin-penetrating sites on the cornea defined using partitioning are subject to curve fitting and noise reduction, so as to obtain the penetration depth of riboflavin and the anterior and posterior corneal surface curves, from which the image processing method can be used to ascertain the penetration depth of riboflavin in the cornea intuitively and accurately.

BRIEF DESCRIPTION OF THE DRAWINGS

For explaining the technical schemes of embodiments of the present invention more clearly, the accompanying drawings referred in the following description of the embodiments will be briefed below. It is apparent that the accompanying drawings listed herein are only intended to present some embodiments of the present invention, and people of ordinary skill in the art are believed to be able to conceive more drawings without creative labor, wherein:

FIG. 1 is a flowchart of a method for detecting a penetration depth of riboflavin in a cornea according to one embodiment of the present invention;

DETAILED DESCRIPTION OF THE INVENTION

Figure 2:
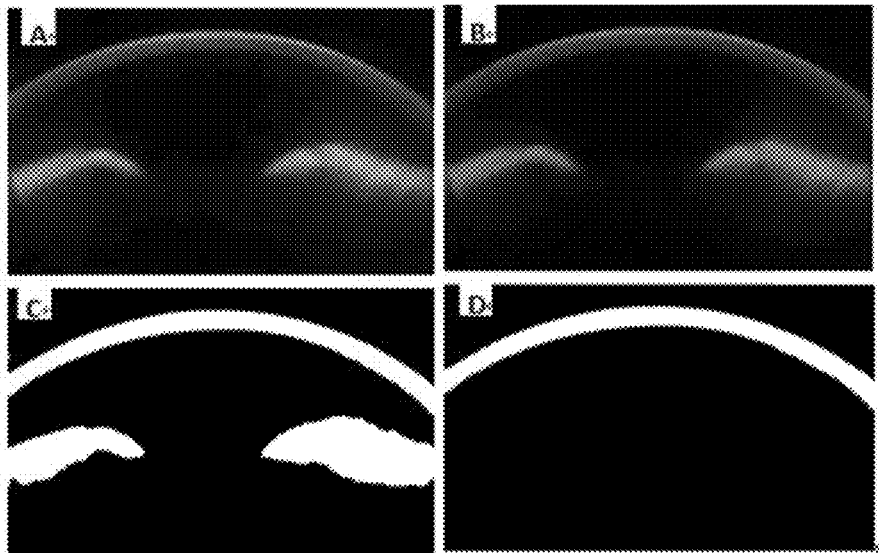
FIG. 2 provides comparison among an optical section of RGB colors, a luminance component L\* image, a post-binarization luminance component L\* image, and a post-Blob image in Step S1 of the method of the embodiment of the present.

To further clarify the objectives, technical schemes, and advantages of the present invention, some embodiments will be detailed with reference to the accompanying drawings.

Figure 1:
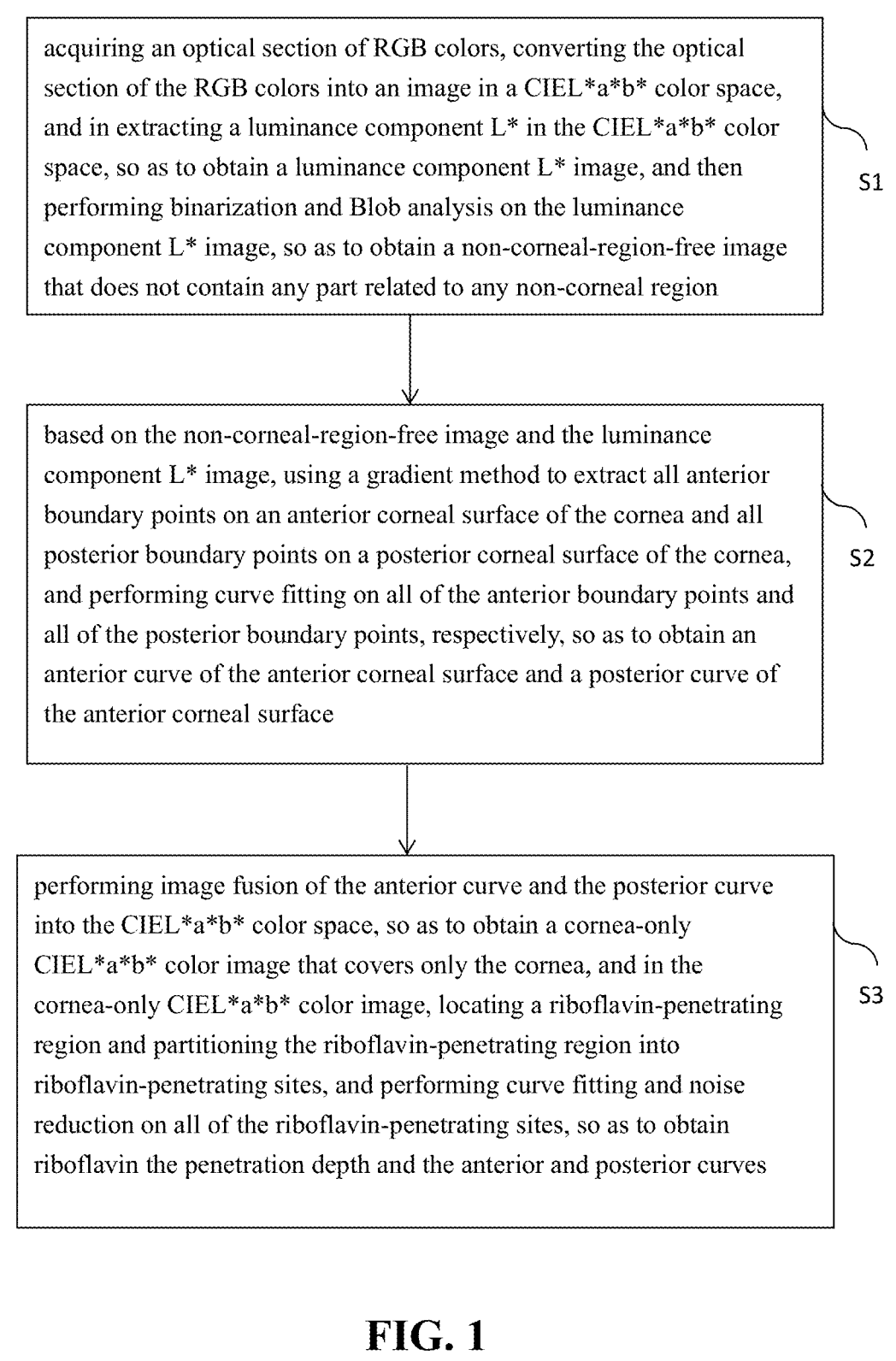

As shown in FIG. 1, in one embodiment, the present invention provides a method for detecting a penetration depth of riboflavin in a cornea. The method comprises the following steps:

Step S1: acquiring an optical section of RGB colors, converting the optical section of the RGB colors into an image in a CIEL\*a\*b\* color space, and in extracting a luminance component L\* in the CIEL\*a\*b\* color space, so as to obtain a luminance component L\* image, and then performing binarization and Blob analysis on the luminance component L\* image, so as to obtain a non-corneal-region-free image that does not contain any part related to any non-corneal region;

Step S2: based on the non-corneal-region-free image and the luminance component L\* image, using a gradient method to extract all anterior boundary points on an anterior corneal surface of the cornea and all posterior boundary points on a posterior corneal surface of the cornea, and performing curve fitting on all of the anterior boundary points and all of the posterior boundary points, respectively, so as to obtain an anterior curve of the anterior corneal surface and a posterior curve of the anterior corneal surface; and Step S3: performing image fusion of the anterior curve and the posterior curve into the CIEL\*a\*b\* color space, so as to obtain a cornea-only CIEL\*a\*b\* color image that covers only the cornea, and in the cornea-only CIEL\*a\*b\* color image, locating a riboflavin-penetrating region and partitioning the riboflavin-penetrating region into riboflavin-penetrating sites, and performing curve fitting and noise reduction on all of the riboflavin-penetrating sites, so as to obtain riboflavin the penetration depth and the anterior and posterior curves.

Specifically, in the Step S1, an optical section of RGB colors is first acquired using a slit lamp that is commonly used for ophthalmologic examinations.

Secondary, since selection of the color space is significant to portioning of color images. With different color spaces selected, the applicable algorithms can be very different. Herein, the CIEL\*a\*b\* color space is used as to optimal selection. In this color space, colors are denoted with three components, wherein L\* represents the luminance of the image, a\* represents the range from red to green, and b\* represents the range from yellow to blue.

As direct conversion between the CIEL\*a\*b\* color space and the RGB space is infeasible, intermediate conversion to the CIE-XYZ color space is necessary. A CIE-XYZ color space model provides a color space built according to the perceptual metric of human eyes to colors, and is the basis for almost all color space models. A CIE-XYZ model regards human eyes as a receiver for the three primary colors (red, green, and blue), and all colors are perceived as results of "excitation" by the three primary colors with different proportions. X, Y, and Z are defined as the excitation amounts (intensities) of red, green, and blue, respectively, all in range [0,1]. Therefore, the optical section of RGB colors is first converted into an image in the CIE-XYZ color space and then converted into an image in the CIEL\*a\*b\* color space.

Therein, and when a CIE standard light source D65 is used, conversion of the optical section between the CIE-XYZ color space and the RGB color space is expressed in Equation (1):

$$\begin{pmatrix} X \\ Y \\ Z \end{pmatrix} = \begin{pmatrix} 0.412453 & 0.357580 & 0.180423 \\ 0.212671 & 0.715160 & 0.072169 \\ 0.019334 & 0.119193 & 0.950227 \end{pmatrix} * \begin{pmatrix} R \\ G \\ B \end{pmatrix}. \tag{1}$$

A major issue about the CIE-XYZ color space is its non-uniformness. For example, a great chromatic aberration in the green interval in the chromaticity diagram is almost unperceivable to human eyes, yet a small chromatic aberration in the purple interval is obvious to human eyes. This is adverse to standardized measurement of chromatic aberrations. To solve this problem, a uniform color space model named CIEL\*a\*b\* was developed.

Herein, the term "uniform" describes a state that even changes in a value incurs even changes in human sense. In addition, a main feature of the CIEL\*a\*b\* color space is that inter-color distances correspond to Euclidean distances. That is, the color difference between two pixels with a small distance therebetween is small, and the color difference between two pixels with a large distance therebetween is large. This property is particularly advantageous to the subsequent step for image partitioning. According to features of the image actually acquired, human eyes can clearly identify the anterior and posterior corneal boundaries as well as the color variations in the corneal stroma happening when riboflavin enters the corneal stroma. For these reasons, the CIEL\*a\*b\* color space is the optimal selection.

Therein, a conversion relation between the CIEL\*a\*b\* color space and the CIE-XYZ color space is expressed in Equation (2):

$$L^* = \begin{cases} 116 * \sqrt[3]{\dfrac{Y}{Y_n}} - 16 & \left(\dfrac{Y}{Y_n} > 0.008856\right) \\ 903.25 * \dfrac{Y}{Y_n} & \left(\dfrac{Y}{Y_n} \leq 0.008856\right) \end{cases} \tag{2}$$

$$a^* = 500\left[f\left(\frac{X}{X_n}\right) - f\left(\frac{Y}{Y_n}\right)\right]$$

$$b^* = 200\left[f\left(\frac{Y}{Y_n}\right) - f\left(\frac{Z}{Z_n}\right)\right]$$

where, if t>0.008856, f(t)=

$$\sqrt[3]{t}$$

; otherwise f(t)=7.787\*t; and when a CIE standard light source D65 is used, $X_n$=94.81, $Y_n$=100.00, $Z_n$=107.304.

Then the L\* component in CIE L\*a\*b\* is extracted, so as to obtain a luminance component L\* image. At this time, the luminance component L\* image may be processed as a normal 8-digit grey-scale image.

Afterward, the threshold for binarization is determined using gray statistics and binarization is performed according to the threshold. To this end, one approach is: Threshold=Mean Grey Level+α\*Grey Level Variance, where α is a parameter determined according to real images of the cornea collected in different environments at different time points, and may be positive or negative.

At last, Blob analysis is performed on the binarized image, so as to obtain the non-corneal-region-free image. Since the cornea is at the center in the image and covers the most part of the width of the image with a substantive area, non-corneal regions can be easily located and excluded using Blob analysis according to the information of the area and the location.

As shown in FIG. 2, A is the original RGB image, B is the luminance component L\* image in the CIEL\*a\*b\* color space, C is the image after binarization, and D is the cornea-only image obtained through Blob analysis.

Figure 3:
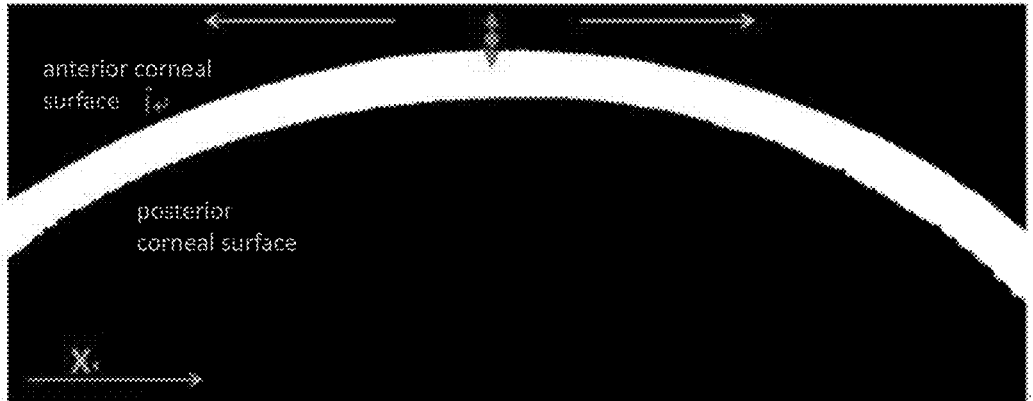
FIG. 3 is a partial, close-up view of Image D in FIG. 2.

In Step S2, in the non-corneal-region-free image (D in FIG. 2) obtained in Step S1, the corresponding boundary of the anterior corneal surface is located based on the midpoint of the X axis (i.e., the corneal direction) as the starting point (as shown in FIG. 3), and a line is drawn in the luminance component L\* image (B in FIG. 2). Then the gradient method is used to obtain the gradient jump related to every point on the line. Therein, the point corresponding to the maximum value is the actual boundary point along the drawn line. This boundary point is more precise than the boundary obtained using binarization. The same is repeated in the arrow direction, so as to obtain actual boundary points along the drawn line as all the anterior boundary points.

Similarly, in the non-corneal-region-free image (D in FIG. 2) obtained in Step S1, the corresponding boundary of the posterior corneal surface is located based on the midpoint of the X axis (i.e., the corneal direction) as the starting point, and a line is drawn in the luminance component L\* image (B in FIG. 2). Then the gradient method is used to obtain the gradient jump related to every point on the line. Therein, the point corresponding to the maximum value is the actual boundary point along the drawn line. This boundary point is more precise than the boundary obtained using binarization. The same is repeated in the arrow direction, so as to obtain actual boundary points along the drawn line as all the posterior boundary points.

At last, performing polynomial fitting based on a least squares method on both of all the anterior boundary points and all the posterior boundary points, so as to obtain the curves of the anterior and the posterior corneal surfaces. Curve fitting is helpful to eliminate some noise-incurred imprecise boundary points. It is to be noted that effect of curve fitting may be alternatively be achieved in other ways.

Figure 4:
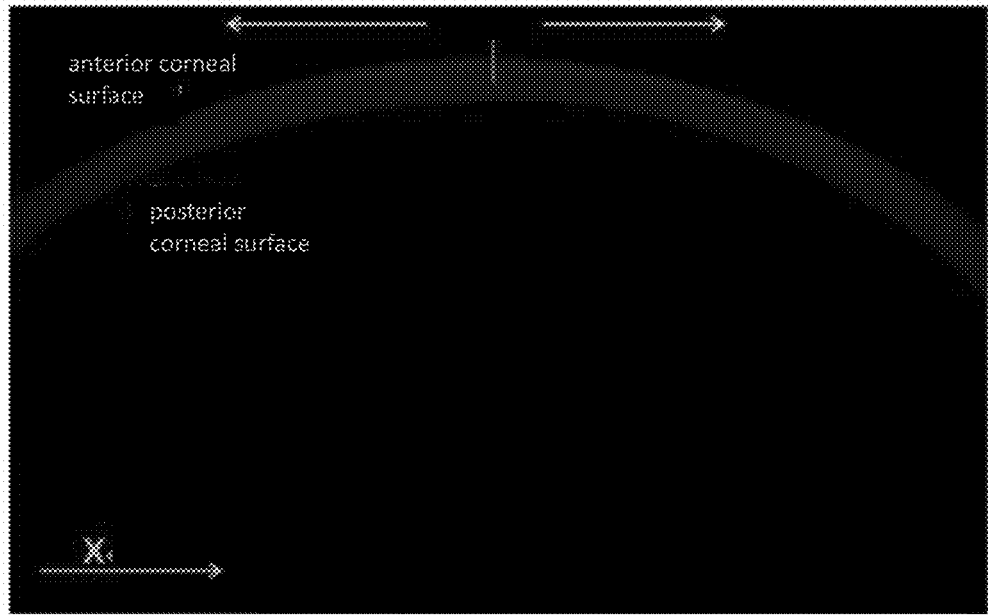
FIG. 4 is a CIEL\*a\*b color image of the corneal region according to one embodiment of the present invention.

Step S3 is about using a minimum method to perform image fusion of the anterior curve and the posterior curve into the CIEL*a*b* color space, so as to obtain a cornea-only CIEL*a*b* color image that covers only the cornea, as shown in FIG. 4.

Then in the cornea-only CIEL*a*b* color image, the riboflavin-penetrating region that divides each of superior and inferior corneal surfaces into two parts is located. As shown in FIG. 4, each of the superior and inferior corneal surfaces can be divided into two parts. The blue area is where the photosensitizer, i.e., riboflavin, penetrates. Since the image is in the CIEL*a*b* color space, differences between colors are in proportion to Euclidean distances between components in the color space. In other words, pixel points having a small distance therebetween have a small color difference therebetween, and pixel points having a large distance therebetween have a large color difference therebetween.

Then a K-mean clustering algorithm is used to partition the riboflavin-penetrating region, so as to obtain the riboflavin-penetrating sites. This algorithm is one of the simplest clustering methods. It is about identifying K cluster centers using the iterative method, and assigning every data point to the nearest cluster center, so that the sum of squares of the distances from the points to the corresponding cluster centers is the minimum. In the present instance there are only two types, i.e., K=2.

It is to be noted that the line-drawing method may be used instead (with superior precision and robustness). As shown in FIG. 4. a red line is drawn from the superior corneal surface to the inferior corneal surface. The K-mean algorithm is only used for pixel values corresponding to the drawn line to determine the coordinates of the optimal boundary point through partitioning, namely the penetration point. Then the red line is moved along the directions of the yellow arrows, thereby determining the coordinates of the boundary point at every location.

At last, curve fitting and noise reduction are performed on all riboflavin-penetrating sites, so as to obtain riboflavin the penetration depth and the anterior and posterior curves.

Figure 5:
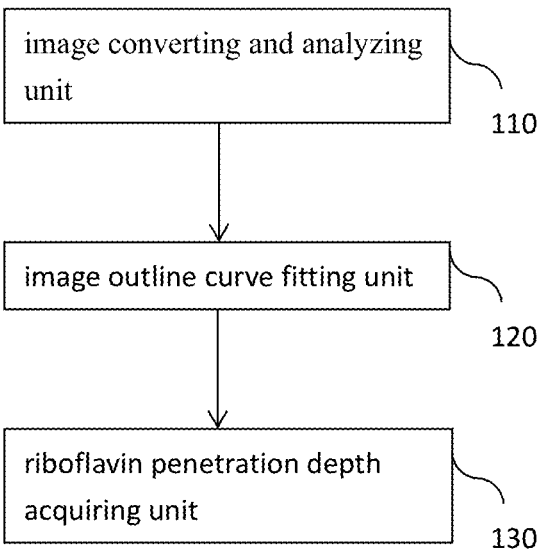
FIG. 5 is a structural diagram of an apparatus for detecting a penetration depth of riboflavin in a cornea according to another embodiment of the present invention.

As shown in FIG. 5, in an embodiment, the present invention provides an apparatus for detecting a penetration depth of riboflavin in a cornea. The apparatus comprises:

an image converting and analyzing unit 110, for acquiring an optical section of RGB colors, converting the optical section of the RGB colors into an image in a CIEL*a*b* color space, and in extracting a luminance component L* in the CIEL*a*b* color space, so as to obtain a luminance component L* image, and then performing binarization and Blob analysis on the luminance component L* image, so as to obtain a non-corneal-region-free image that does not contain any part related to any non-corneal region;

an image outline curve fitting unit 120, for, based on the non-corneal-region-free image and the luminance component L* image, using a gradient method to extract all anterior boundary points on an anterior corneal surface of the cornea and all posterior boundary points on a posterior corneal surface of the cornea, and performing curve fitting on all of the anterior boundary points and all of the posterior boundary points, respectively, so as to obtain an anterior curve of the anterior corneal surface and a posterior curve of the anterior corneal surface; and a riboflavin penetration depth acquiring unit 130, for performing image fusion of the anterior curve and the posterior curve into the CIEL*a*b* color space, so as to obtain a cornea-only CIEL*a*b* color image that covers only the cornea, and in the cornea-only CIEL*a*b* color image, locating a riboflavin-penetrating region and partitioning the riboflavin-penetrating region into riboflavin-penetrating sites, and performing curve fitting and noise reduction on all of the riboflavin-penetrating sites, so as to obtain riboflavin the penetration depth and the anterior and posterior curves.

Therein, the optical section of the RGB color is acquired using a slit lamp.

Implementation of the embodiments of the present invention provides the following beneficial effects:

In the present invention, an optical section is acquired using a slit lamp that is commonly used for ophthalmologic examinations. Then the acquired RGB color image is converted into the CIEL*a*b* color space. The luminance component L* is extracted for binarization and Blob analysis, so as to extract the region showing the cornea. Afterward, the exact boundaries of the anterior and posterior corneal surfaces are located using the gradient method and curve fitting is performed. The result is fused into the CIEL*a*b* color space to provide a CIEL*a*b* color image covering only the cornea. At last, riboflavin-penetrating sites on the cornea defined using partitioning are subject to curve fitting and noise reduction, so as to obtain the penetration depth of riboflavin and the anterior and posterior corneal surface curves, from which the image processing method can be used to ascertain the penetration depth of riboflavin in the cornea intuitively and accurately.

It is to be noted that in the embodiment proposing the apparatus, the functional partition among the individual units is based on exemplificative logic, and is not limiting. Other arranges may be feasible as long as the corresponding functions can be achieved. In addition, the denominations assigned to the individual units are for convenient differentiation, and shall by no means limit the scope of the present invention.

As will be appreciated by people of ordinary skill in the art, all or a part of the steps of the method in the foregoing embodiment may be accomplished by means of hardware under instructions from programs that may be stored in a computer-readable medium, such as a ROM/RAM, a magnetic disk, an optical disk, etc.

The present invention has been described with reference to the preferred embodiments and it is understood that the embodiments are not intended to limit the scope of the present invention. Moreover, all equivalent changes or modifications which do not depart from the concept of the present invention should be encompassed by the appended claims. Hence, the scope of the present invention shall only be defined by the appended claims.

What is claimed is:

1. A method for detecting a penetration depth of riboflavin in a cornea, the method comprising steps of:

Step S1: acquiring an optical section of RGB colors, converting the optical section of the RGB colors into an image in a CIEL*a*b* color space, and in extracting a luminance component L* in the CIEL*a*b* color space, so as to obtain a luminance component L* image, and then performing binarization and Blob analysis on the luminance component L* image, so as to obtain a non-corneal-region-free image that does not contain any part related to any non-corneal region;

Step S2: based on the non-corneal-region-free image and the luminance component L* image, using a gradient method to extract all anterior boundary points on an anterior corneal surface of the cornea and all posterior boundary points on a posterior corneal surface of the cornea, and performing curve fitting on all of the anterior boundary points and all of the posterior boundary points, respectively, so as to obtain an anterior curve of the anterior corneal surface and a posterior curve of the anterior corneal surface; and Step S3: performing image fusion of the anterior curve and the posterior curve into the CIEL*a*b* color space, so as to obtain a cornea-only CIEL*a*b* color image that covers only the cornea, and in the cornea-only CIEL*a*b* color image, locating a riboflavin-penetrating region and partitioning the riboflavin-penetrating region into riboflavin-penetrating sites, and performing curve fitting and noise reduction on all of the riboflavin-penetrating sites, so as to obtain riboflavin the penetration depth and the anterior and posterior curves.

2. The method of claim 1, wherein the optical section of the RGB colors in Step S1 is first converted into a CIE-XYZ color space and then converted into the CIEL*a*b* color space.

3. The method of claim 2, wherein conversion of the optical section between the CIE-XYZ color space and the RGB color space is expressed in Equation (1):

$$\begin{pmatrix} X \\ Y \\ Z \end{pmatrix} = \begin{pmatrix} 0.412453 & 0.357580 & 0.180423 \\ 0.212671 & 0.715160 & 0.072169 \\ 0.019334 & 0.119193 & 0.950227 \end{pmatrix} * \begin{pmatrix} R \\ G \\ B \end{pmatrix}. \quad (1)$$

4. The method of claim 3, wherein a conversion relation between the CIEL*a*b* color space and the CIE-XYZ color space is expressed in Equation (2):

$$L^* = \begin{cases} 116 * \sqrt[3]{\dfrac{Y}{Y_n}} - 16 & \left(\dfrac{Y}{Y_n} > 0.008856\right) \\ 903.25 * \dfrac{Y}{Y_n} & \left(\dfrac{Y}{Y_n} \le 0.008856\right) \end{cases} \quad (2)$$

$$a^* = 500\left[ f\left(\dfrac{X}{X_n}\right) - f\left(\dfrac{Y}{Y_n}\right) \right]$$

$$b^* = 200\left[ f\left(\dfrac{Y}{Y_n}\right) - f\left(\dfrac{Z}{Z_n}\right) \right]$$

where, if t>0.008856, f(t)=

$$\sqrt[3]{t}$$

; otherwise f(t)=7.787*t; and when a CIE standard light source D65 is used, $X_n$=94.81, $Y_n$=100.00, $Z_n$=107.304.

5. The method of claim 1, wherein the Step S2 comprises:

in the non-corneal-region-free image, based on a midpoint of an X axis as a starting point, locating a corresponding anterior corneal surface boundary, drawing a line in the luminance component L* image correspondingly, and further using the gradient method, so as to obtain actual boundary points along the drawn line as all the anterior boundary points;

in the non-corneal-region-free image, based on the midpoint of the X axis as the starting point, locating a corresponding posterior corneal surface boundary, drawing a line in the luminance component L* image correspondingly, and further using the gradient method, so as to obtain actual boundary points along the drawn line as all the posterior boundary points; and performing polynomial fitting based on a least squares method on both of all the anterior boundary points and all the posterior boundary points, so as to obtain the anterior curve and the posterior curve.

6. The method of claim 1, wherein the Step S3 comprises:

using a minimum method to perform image fusion of the anterior curve and the posterior curve into the CIEL*a*b* color space, so as to obtain the cornea-only CIEL*a*b* color image;

in the cornea-only CIEL*a*b* color image, locating the riboflavin-penetrating region that divides each of superior and inferior corneal surfaces into two parts;

using a K-mean clustering algorithm to partition the riboflavin-penetrating region, so as to obtain the riboflavin-penetrating sites; and performing the curve fitting and the noise reduction on all the riboflavin-penetrating sites, so as to obtain the penetration depth and the anterior and posterior curves.

7. The method of claim 1, wherein the optical section of the RGB colors in Step S1 is acquired using a slit lamp.

8. An apparatus for detecting a penetration depth of riboflavin in a cornea, the apparatus comprising:

an image converting and analyzing unit, for acquiring an optical section of RGB colors, converting the optical section of the RGB colors into an image in a CIEL*a*b* color space, and in extracting a luminance component L* in the CIEL*a*b* color space, so as to obtain a luminance component L* image, and then performing binarization and Blob analysis on the luminance component L* image, so as to obtain a non-corneal-region-free image that does not contain any part related to any non-corneal region;

an image outline curve fitting unit, for, based on the non-corneal-region-free image and the luminance component L* image, using a gradient method to extract all anterior boundary points on an anterior corneal surface of the cornea and all posterior boundary points on a posterior corneal surface of the cornea, and performing curve fitting on all of the anterior boundary points and all of the posterior boundary points, respectively, so as to obtain an anterior curve of the anterior corneal surface and a posterior curve of the anterior corneal surface; and a riboflavin penetration depth acquiring unit, for performing image fusion of the anterior curve and the posterior curve into the CIEL*a*b* color space, so as to obtain a cornea-only CIEL*a*b* color image that covers only the cornea, and in the cornea-only CIEL*a*b* color image, locating a riboflavin-penetrating region and partitioning the riboflavin-penetrating region into riboflavin-penetrating sites, and performing curve fitting and noise reduction on all of the riboflavin-penetrating sites, so as to obtain riboflavin the penetration depth and the anterior and posterior curves.

9. The apparatus of claim 8, wherein the optical section of the RGB colors is acquired using a slit lamp.

* * * * *